United States Patent [19]

Yamahira et al.

[11] Patent Number: 5,385,738
[45] Date of Patent: * Jan. 31, 1995

[54] SUSTAINED-RELEASE INJECTION

[75] Inventors: Yoshiya Yamahira, Kobe; Keiji Fujioka, Amagasaki; Shigeji Sato, Ibaraki; Yoshihiro Takada, Takatsuki, all of Japan

[73] Assignee: Sumitomo Pharmaceuticals Company, Ltd., Osaka, Japan

[ * ] Notice: The portion of the term of this patent subsequent to Sep. 27, 2005 has been disclaimed.

[21] Appl. No.: 844,929

[22] Filed: Mar. 4, 1992

Related U.S. Application Data

[63] Continuation of Ser. No. 488,531, Feb. 28, 1990, abandoned, which is a continuation of Ser. No. 849,968, Apr. 10, 1986, abandoned, which is a continuation-in-part of Ser. No. 660,044, Oct. 12, 1984, abandoned.

[30] Foreign Application Priority Data

| Oct. 14, 1983 | [JP] | Japan | 58-193064 |
| Nov. 1, 1983 | [JP] | Japan | 58-206226 |
| Nov. 21, 1983 | [JP] | Japan | 58-220452 |
| Apr. 11, 1985 | [JP] | Japan | 60-77250 |

[51] Int. Cl.[6] .................. A61K 9/14; A61K 9/50; A61F 2/02; B01J 13/02
[52] U.S. Cl. ........................ 424/489; 424/423; 424/424; 424/426; 424/499; 428/402.2; 428/402.24; 514/801; 514/953; 514/963; 514/964; 514/965; 264/4.1
[58] Field of Search .......... 424/85.4, 85.5, 85.6, 424/85.7, 422, 423, 424, 426, 489, 499; 514/801, 953, 963, 964, 965; 264/4.1; 428/402.2, 402.24

[56] References Cited

U.S. PATENT DOCUMENTS

| 2,518,510 | 8/1950 | Welch et al. | 424/78 |
| 3,016,895 | 1/1962 | Sein | |
| 3,857,932 | 12/1974 | Shepherd et al. | |
| 4,181,731 | 1/1980 | Yoshida et al. | |
| 4,191,741 | 3/1980 | Hudson et al. | 424/19 |
| 4,245,635 | 1/1981 | Kontos | |
| 4,347,234 | 8/1982 | Wahlig et al. | |
| 4,376,765 | 3/1983 | Trouet et al. | 514/12 |
| 4,442,051 | 4/1984 | Rowe et al. | |
| 4,465,622 | 8/1984 | Nobuhara et al. | 424/85 |
| 4,474,753 | 10/1984 | Haslam et al. | 424/85 |
| 4,503,035 | 3/1985 | Pestka et al. | 424/85 |
| 4,507,281 | 3/1985 | Asculai et al. | 424/85 |
| 4,536,387 | 8/1985 | Sakamoto et al. | |
| 4,604,284 | 8/1986 | King et al. | 530/351 |
| 4,609,546 | 9/1986 | Hiratani | 424/85 |
| 4,855,134 | 8/1989 | Yamahira et al. | 424/85.7 |

FOREIGN PATENT DOCUMENTS

| 0094157 | 11/1983 | European Pat. Off. |
| 0098110 | 1/1984 | European Pat. Off. |
| 0134289 | 3/1985 | European Pat. Off. |
| 102519 | 8/1980 | Japan |
| 642385 | 11/1950 | United Kingdom |
| 1567503 | 5/1980 | United Kingdom |
| 2042888 | 10/1980 | United Kingdom |
| 2067072 | 7/1981 | United Kingdom |
| 2091554 | 1/1982 | United Kingdom |
| 83/01198 | 4/1983 | WIPO |

Primary Examiner—G. S. Kishore
Assistant Examiner—C. Azpuru
Attorney, Agent, or Firm—Birch, Stewart, Kolasch & Birch

[57] ABSTRACT

The present invention relates to a sustained-release injection, which comprises a suspension of a powder comprising an active ingredient and a pharmaceutically acceptable biodegradable carrier (e.g. proteins, polysaccharides and synthetic high molecular compounds, preferably collagen, atelocollagen, gelatin, and a mixture thereof) in a viscous solvent for injection (e.g. vegetable oils, polyethylene glycol, propylene glycol, silicone oil, and medium-chain fatty acid triglycerides). The sustained-release injection can release the active ingredient at an effective level for a long period of time when injected.

33 Claims, 1 Drawing Sheet

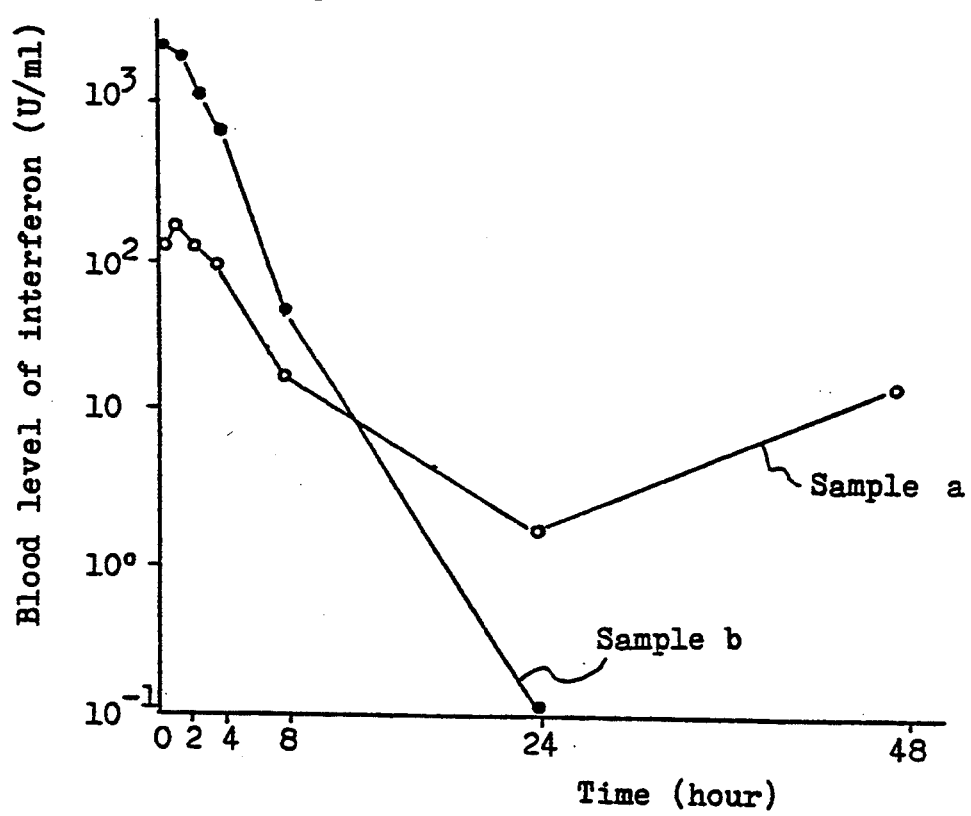

SUSTAINED-RELEASE INJECTION

This application is a continuation of application Ser. No. 07/488,531 filed on Feb. 28, 1990, now abandoned, which is a continuation application of Ser. No. 06/849,968 filed on Apr. 10, 1986, now abandoned, which is a continuation in part application of Ser. No. 660,044 filed Oct. 12, 1984, now abandoned.

The present invention relates to a sustained-release injection. More particularly, it relates to a sustained-release injection which comprises a suspension of a powder comprising an active ingredient and a pharmaceutically acceptable biodegradable carrier in a viscous solvent for injection. The preparation of the invention is particularly suitable for medicaments which are unstable to heat.

It is known that a sustained-release injection is prepared by dissolving or suspending an active ingredient in polyethylene glycol, an oil for injection or gelatin solution, but these known preparations are not satisfactory and can not be applied to a water-soluble medicament which is effective in a small amount. Besides, although a preparation using a non-biodegradable carrier such as silicone is recently used as a sustained-release preparation in some medical sections, it is not preferable because when it is administered in a parenteral route, there is a problem of accumulation of the carrier.

It has been very desirable to make various medicaments in the form of a sustained-release injection, because the pharmaceutical activities of the medicaments will be potentiated in such a preparation, and hence, it is useful to develop a sustained-release injection of medicaments.

The present inventors have conducted intensive studies directed to an improved sustained-release injection of medicaments, and have found that a desired sustained-release injection can be obtained by admixing an active ingredient with a specific biodegradable carrier and suspending the powdery mixture in a viscous solvent for injection.

An object of the present invention is to provide an improved sustained-release injection. Another object of the invention is to provide a suspension type, sustained-release injection which can release the active ingredient and can maintain the desired level of the active ingredient in blood or in a lesional region for a long period of time. A further object of the invention is to provide a method for preparing the sustained-release preparation as set forth above without using any specific binding agent and without heating. These and other objects and advantages of the present invention will be apparent to persons skilled in the art from the following description.

The sustained-release injection of the present invention is a suspension type preparation, which comprises a powdery mixture of an active ingredient and a pharmaceutically acceptable biodegradable carrier, which is suspended in a viscous solvent for injection.

The biodegradable carrier used in the present invention means a carrier which can easily be absorbed or can be subjected to enzymolysis in the body and can be implanted into the body. Suitable examples of the biodegradable carrier are proteins such as collagen, gelatin, albumin; polysaccharides such as chitins; and synthetic high molecular compounds such as polyglycolic acid, polylactic acid, polyglutamic acid, or the like. These substances can be used alone or in any combination of two or more thereof, but in view of safety and easy handling, proteins such as collagen, gelatin, albumin or a mixture thereof are preferable. Particularly preferred carrier is collagen or gelatin or a mixture thereof in view of the good moldability thereof. Collagen is a protein which is a main protein of connective tissue of animals and has less antigenicity, and hence, has widely been used as a safe operation yarn in various medical operations. The collagen may be an atelocollagen having far less antigenicity which is obtained by removing the telopeptide region by treating collagen with an enzyme (e.g. pepsin) in order to make it safer. Gelatin is a protein derived from collagen. Gelatin is a high molecular weight amphoteric electrolyte which has less antigenicity is convertible between sol and gel forms and is cheap in cost, and hence it has already been confirmed as a safe substance for medical use.

The active ingredient used in the present invention is not specified, but includes particularly water-soluble medicaments which are hardly prepared in the form of a sustained-release injection by a conventional method, for example, anti-tumor antibiotics such as mitomycin, bleomycin, adriamycin etc.; low molecular weight compounds such as indomethacin, 4-carbamoyl-5-hydroxyimidazole (SM-108) or a salt or a hydrate thereof, prostaglandins, prostacyclines, tespamin, etc.; high molecular weight compounds such as tissue plasminogen activator, etc.; various bio-hormones; and further interferons, interleukins, tumor necrosis factor, and some other cytokines (e.g. macrophage activating factor, migration inhibitory factor, colony stimulating factor, etc.).

More preferably, the medicaments are those which are unstable to heat, for example, tissue plasminogen activator, prostaglandins, prostacyclines, various bio-hormones, interferons, interleukins, tumor necrosis factor, and some other cytokines (e.g. macrophage activating factor, migration inhibitory factor and colony stimulating factor). The bio-hormones are substances which are produced within the living body and regulate the bio-functions, and include growth hormone (GH) such as human growth hormone (HGH), bovine growth hormone (bGH) including biosynthetic product (B-HGH, etc.); growth hormone releasing factors (GRF) which are known as peptides consisting of a number of amino acids of 44, 40, 37 or 29 (e.g. hGRF(1–44)NH$_2$, hGRF(1–29)NH$_2$); somatomedines (SM) such as SM-A, SM-B, SM-C, insulin-like growth factor (IGF)-I, IGF-II, and multiplication stimulating activity (MSA); and calcitonin (i.e. calcium regulating hormone secreted from the mammalian thyroid gland and in non-mammalian species from the ultimobranchial gland).

Among the above medicaments, prostaglandins, prostacyclines, various bio-hormones, mitomycin, tespamin, interferons, interleukins, tumor necrosis factor, tissue plasminogen activator, and some other cytokines etc. are very unstable not only within a body but also in the form of a preparation, and hence the activity thereof is largely and rapidly decreased by the conventional release-sustaining techniques such as heat treatment or irradiation, or chemical treatments with organic solvents or aldehydes. Moreover, since these medicaments are water-soluble and are used in a very small amount, it is very difficult to prepare sustained-release preparation thereof by a conventional method. Various interferons, interleukins, tumor necrosis factor and some other cytokines are somewhat different from each other, but are common in that they have very similar molecular weights and are glycoprotein or protein and have similar pharmacological and physicochemical properties as compared to those of α-interferon as shown in the experiment disclosed hereinafter; and all of these compounds are prepared in the desired excellent sustained-release injection of the present invention.

The above medicaments can be used as the active ingredient alone or in a combination of two or more thereof.

The medicaments and carriers used in the present invention are preferably purified products in order to enhance the release-sustaining properties, but commercially available products may be used as is. The commercially available medicaments and carriers usually contain some appropriate additives such as stabilizers and buffering agents to some extent. For instance, an aqueous collagen solution contains usually a buffer of inorganic or organic salts, such as a phosphate buffer, citrate buffer or acetate buffer. Commercially available interferons usually contain sodium chloride and further human serum albumin, amino acids (e.g. glycine, alanine, etc.), succharides (e.g. glucose, etc.), sugar-alcohols (e.g. mannitol, xylitol, etc.). Other medicaments contain occasionally fetal cow serum, bovine serum albumin, phosphate buffered saline, Tris, etc. These products may be used as is, but in view of release-sustaining properties, it is preferable to remove such additives or other components in order to enhance the release-sustaining properties.

The viscous solvent used for suspending the powder of the active ingredient and the biodegradable carrier include all conventional solvents for injection, such as vegetable oils, polyethylene glycol, propylene glycol, silicone oil, medium-chain fatty acid triglycerides, or the like. Suitable examples of the vegetable oils are peanut oil, cotton seed oil, sesame oil, castor oil, olive oil, corn oil, iodinated poppy seed oil fatty acids ethyl esters, or the like.

The preparation of the present invention contains the active ingredient in an amount in which the active ingredient is usually used. For example, indomethacin is usually contained in an amount of 0.5 to 500 mg, preferably 1 to 200 mg, per dosage unit, and interferon is usually contained in an amount of $10^4$ to $10^9$ IU, preferably $10^5$ to $5 \times 10^8$ IU, per dosage unit, and SM-108 or a salt or hydrate thereof is usually contained in an amount of 1 mg to 2 g, preferably 10 mg to 1 g, per dosage unit.

Besides, the ratio of the medicament and the carrier is not specified, but, for example, indomethacin is preferably incorporated in an amount of 0.005 to 10 mg per 1 mg of the carrier, and interferon is preferably incorporated in an amount of $10^3$ to $10^8$ IU per 1 mg of the carrier, and SM-108 is preferably incorporated in an amount of 0.01 to 1 mg per 1 mg of the carrier.

The sustained-release injection of the present invention is prepared in the following manner.

First, a powder of an active ingredient contained in a biodegradable carrier is prepared, and the powder is suspended in a viscous solvent for injection. The preparation of the powder can be done by any method which the active ingredient is incorporated in the carrier. For instance, when the medicaments are unstable to heat or to organic solvents and it is desired to enhance the release-sustaining properties, it is preferable to use proteins such as collagen, gelatin, albumin or a mixture thereof. In this case, it is prepared by mixing the active ingredient or an aqueous solution thereof in a biodegradable carrier or an aqueous solution thereof (i.e. by admixing an active ingredient and a carrier in the state of a liquid), drying the mixture and then pulverizing. The drying method is not specified, but it may be dried, for example, by allowing to stand, or by spray-drying or lyophilization. Besides, in the case of using a medicament unstable to heat as the active ingredient, it is preferable not to heat the mixture during any of the steps. That is, in the above steps, the mixing step and drying step are usually carried out at room temperature or at a lower temperature and optionaly under cooling. For instance, the mixing step is usually carried out at about 5° C. to 30° C.; the drying by lyophilization is usually carried out at −50° C. to 0° C.; and the drying by allowing to stand or by spray-drying is usually carried out at room temperature or lower (i.e. about 15° C. to 30° C.). Besides, the spray-drying is usually carried out by controlling the temperature of the solution and vessel at room temperature or lower, by which the temperature of the active ingredient can be kept at room temperature or lower and hence no damage is given to the active ingredient even though it is unstable to heat. The preparation thus obtained is optionally pulverized into powders under cooling with dry ice or liquid nitrogen so that the preparation is kept at about −10° C. to about −100° C., or by any other conventional pulverization methods at room temperature or lower temperature.

The pulverized product having an injectable particle size (e.g. 0.1 to 1000 μm) is then suspended in a viscous solvent for injection to give a sustained-release suspension for injection. Alternatively, the pulverized product and the viscous solvent may be packed in the form of a kit, and they are mixed to prepare a suspension for injection when used.

In the sustained-release injection preparation of the present invention, the active ingredient is incorporated into the biodegradable carrier in the following state:

(i) the active ingredient is chemically bound to the carrier matrix, (ii) The active ingredient is bound to the carrier matrix by intermolecular action, or (iii) The active ingredient is physically embraced within the carrier matrix.

In the preparation, there may optionally be incorporated conventional pharmaceutically acceptable additives such as stabilizers, preservatives, local anesthetic agents, and some agents for aiding formability into special shapes of preparations or release-sustaining of the active ingredient. These additives are not specified, but suitable examples of the agents for aiding formability are methylcellulose, ethylcellulose, hydroxypropylcellulose, polyvinylpyrrolidone, glycolic acid-lactic acid copolymer, polyethylene glycol, propylene glycol, ethyl alcohol, or the like. Suitable examples of the agents for aiding release-sustaining of the active ingredient are cellulose acetate phthalate, ethylcellulose, methylcellulose, hydroxy-propylmethylcellulose, calcium phosphate, lactic acid-glycolic acid copolymer, corn starch, rice starch, potato starch, cellulose, arginates, or the like.

The preparation of the present invention consists preferably, substantially of an active ingredient, a biodegradable carrier and a viscous solvent in order to further enhance the release-sustaining properties. That is, when other components than the active ingredient, carrier and viscous solvent are present in the preparation of the invention, they occasionally promote the release of active ingredient, and hence, it is preferable not to incorporate such other components as much as possible. Accordingly, the present invention has an advantage that the desired sustained-release preparation can be obtained without using any specific binding agent. However, from a practical viewpoint, the preparation may contain other components which are present in the commercially available medicaments and carriers unless they affect substantially the release-sustaining properties. Likewise, the preparation of the invention may optionally incorporate pharmaceutically acceptable conventional additives, unless they affect substantially on the release-sustaining properties.

All steps for the above preparation should be carried out under sterilized conditions because the preparations are used as an injection.

Thus, according to the present invention, the medicaments which are water-soluble and effective in a very small amount are embraced within a carrier which has affinity with the active ingredient and then are suspended in a viscous solvent suitable for injection in the form of a powder, by which there is prepared a sustained-release preparation suitable for injection, which is the novel form of an injection preparation.

The present invention is illustrated by the following Experiment and Examples, but the invention should not be construed to be limited thereto.

EXPERIMENT 1

There were used as the test samples an oily suspension of $\alpha$-interferon-collagen preparation prepared in Example 1 disclosed hereinafter (Sample a) and an aqueous injection of $\alpha$-interferon (originated from Namalwa cells) (Sample b) as a reference. The test samples were each administered intramuscularly to rabbit, and the change of level in blood of the active ingredient with lapse of time was measured by RIA (radioimmunoassay). Two rabbits were used for each sample, and the test samples were each administered in a dose of $10^6$ U/kg. The blood level was shown in an average in two rabbits.

The results are shown in the accompanying FIG. 1. In FIG. 1, o is the graph of Sample a and ⓡ is that of Sample b ($\alpha$-interferon aqueous injection). As is clear from the figure, the sample a showed release-sustaining capabilities, and even after 48 hours, the blood level of several tens unit/ml was maintained.

Thus, it is also suggested by an in vivo test using rabbits that the preparation of the present invention is useful clinically.

EXAMPLE 1

An aqueous solution of $\alpha$-interferon (titer: 4.9 MU/ml) (100 ml) and 2% atelocollagen (50 g) are homogeneously mixed by stirring while preventing the occurrence of foam as much as possible. The mixture is lyophilized and pulverized at a low temperature using liquid nitrogen. The pulverized product thus obtained is suspended in sesame oil to give an oily suspension type, sustained-release preparation wherein interferon is contained in an amount of 4 MU per 1 vial (Sample a).

EXAMPLE 2

An aqueous solution of $\alpha$-interferon (titer: 4.9 MU/ml) (100 ml) and 2% collagen (50 g) are homogeneously mixed by stirring while preventing the occurrence of foam as much as possible. The mixture is lyophilized and pulverized at a low temperature using liquid nitrogen. The pulverized product thus obtained is suspended in sesame oil to give an oily suspension type, sustained-release preparation wherein interferon is contained in an amount of 4 MU per 1 vial.

EXAMPLE 3

An aqueous solution of $\alpha$-interferon (titer, 4.9 MU/ml) (100 ml), 2% atelocollagen (50 g), human serum albumin (150 mg) and thimerosal (120 $\mu$g) are homogeneously mixed while preventing the occurrence of foam as much as possible. The mixture is lyophilized and pulverized at a low temperature using liquid nitrogen. The pulverized product thus obtained is suspended in sesame oil to give an oily suspension type, sustained-release preparation wherein interferon is contained in an amount of 4 MU per 1 vial.

EXAMPLE 4

An aqueous solution of $\alpha$-interferon (titer, 4.9 MU/ml) (100 ml) and gelatin (1 g) are homogeneously mixed at 60° C. while preventing the occurrence of foam as much as possible. The mixture is lyophilized and pulverized at a low temperature using liquid nitrogen. The pulverized product thus obtained is suspended in sesame oil to give an oily suspension type, sustained-release preparation wherein interferon is contained in an amount of 4 MU per 1 vial.

EXAMPLE 5

The pulverized product prepared in the same manner as described in Example 1 is suspended in castor oil to give an oily suspension type, sustained-release preparation wherein interferon is contained in an amount of 4 MU per 1 vial.

EXAMPLE 6

The pulverized product prepared in the same manner as described in Example 1 is suspended in polyethylene glycol to give a suspension type, sustained-release preparation wherein interferon is contained in an amount of 4 MU per 1 vial.

EXAMPLE 7

An aqueous solution of $\alpha$-interferon (titer, 4.9 MU/ml) (100 ml), 2% atelocollagen (50 g) and tespamin (triethylenethiophosphoramide, which is known as an antineoplastic) (245 mg) are homogeneously mixed while preventing the occurrence of foam as much as possible. The mixture is lyophilized and pulverized at a low temperature using liquid nitrogen. The pulverized product thus obtained is suspended in sesame oil to give an oily suspension type, sustained-release preparation wherein interferon and tespamin are contained in an amount of 4 MU and about 2 mg per 1 vial, respectively.

EXAMPLE 8

The pulverized product prepared in the same manner as described in Example 1 is suspended in iodinated poppy seed oil fatty acids ethyl esters (sold by Libiodol Ultra-fluid—Kodama Shoji) to give an oily suspendion type, sustained-release preparation wherein interferon is contained in an amount of 4 MU per 1 vial.

EXAMPLE 9

2% Atelocollagen (75 g) is dissolved in distilled water (300 ml), and thereto are added indomethacin (0.5 g) and arginine (0.292 g). The mixture is lyophilized and pulverized at a low temperature using liquid nitrogen. The pulverized product thus obtained is suspended in sesame oil to give an oily suspension type, sustained-release preparation.

EXAMPLE 10

Gelatin (10 g) is dissolved in distilled water (100 ml) and thereto are added indomethacin (0.5 g), arginine (0.292 g) and 37% formaldehyde (1 ml). The mixture is lyophilized and pulverized at a low temperature using liquid nitrogen. The pulverized product thus obtained is suspended in sesame oil to give an oily suspension type, sustained-release preparation.

EXAMPLE 11

Gelatin (10 g) is dissolved in distilled water (100 ml). To the solution (5 ml) is added hGRF(1–44)NH$_2$ (i.e. human GRF consisting of 44 amino acids) (20 mg), and the mixture is lyophilized. The lyophilized product is pulverized at a low temperature using liquid nitrogen to obtain a powder of GRF - gelatin composite. The powdery composite (100 mg) is suspended in sesame oil (5 ml) to give a sustained-release oily suspension.

EXAMPLE 12

IGF-I (1 mg) is dissolved in a phosphate buffer containing 2% atelocollagen (2 ml), and the solution is lyophilized. The composite thus obtained is pulverized at a low temperature using liquid nitrogen and then suspended in polyethylene glycol (3 ml) to give a sustained-release oily suspension.

EXAMPLE 13

B-HGH (biosynthetic human growth hormone containing glycine 800 mg) (100 IU) is dissolved in 10% aqueous gelatin solution (3 ml) and the solution is lyophilized. The composite thus obtained is pulverized at a low temperature using liquid nitrogen and then suspended in sesame oil (10 ml) to give a sustained-release oily suspension.

EXAMPLE 14

IGF-I (1 mg) is dissolved in a phosphate buffer containing 2% atelocollagen (2 ml), and the solution is lyophilized. The composite thus obtained is pulverized at a low temperature using liquid nitrogen and then suspended in cotton seed oil (5 ml) to give a sustained-release oily suspension.

EXAMPLE 15

B-HGH (biosynthetic human growth hormone containing glycine 800 mg) (100 IU) is dissolved in 10% aqueous gelatin solution (3 ml) and the solution is lyophilized. The composite thus obtained is pulverized at a low temperature using liquid nitrogen, and the pulverized product (100 mg) is suspended in polyethylene glycol (5 ml) to give a sustained-release oily suspension.

What is claimed is:

1. A sustained-release preparation, which comprises a suspension of a powder in an injectable viscous solvent, said powder comprising a pharmaceutically effective amount of an active ingredient and a pharmaceutically acceptable biodegradable carrier selected from the group consisting of proteins, polysaccharides and synthetic high molecular compounds.

2. The preparation according to claim 1, wherein the active ingredient is selected from the group consisting of indomethacin, bio-hormones, interferons, interleukins, tumor necrosis factor, and other cytokines, and the carrier is selected from the group consisting of proteins, polysaccharides, polyglycolic acid, polylactic acid, and polyglutamic acid.

3. The preparation according to claim 1, wherein the active ingredient is selected from the group consisting of indomethacin, bio-hormones, interferons, interleukins, tumor necrosis factor, and other cytokines, and the carrier is selected from the group consisting of collagen, gelatin, albumin, chitins, polyglycolic acid, and polylactic acid.

4. The preparation according to claim 1, wherein the active ingredient is selected from the group consisting of bio-hormones, interferons, interleukins, tumor necrosis factor, and other cytokines.

5. The preparation according to claim 1, wherein the active ingredient is selected from the group consisting of growth hormone, growth hormone releasing factor, somatomedines, and calcitonin.

6. The preparation according to claim 1, wherein the biodegradable carrier is polyalanine and the active ingredient is interferon.

7. The preparation according to claim 1, wherein the biodegradable carrier is albumin and the active ingredient is interferon.

8. The preparation according to claim 1, wherein the biodegradable carrier is polyglutamic acid and the active ingredient is indomethacin.

9. The preparation according to claim 1, wherein the biodegradable carrier is selected from the group consisting of proteins and polysaccharides.

10. The preparation according to claim 1, wherein the biodegradable carrier is selected from the group consisting of collagen, gelatin, albumin and a mixture thereof.

11. The preparation according to claim 1, wherein the viscous solvent for injection is selected from the group consisting of vegetable oils, polyethylene glycol, propylene glycol, silicone oil, and medium-chain fatty acid triglycerides.

12. The preparation according to claim 1, wherein the viscous solvent for injection is selected from the group consisting of peanut oil, cotton seed oil, sesame oil, castor oil, olive oil, corn oil, and iodinated poppy seed oil fatty acid ethyl esters.

13. The preparation according to claim 1, wherein the viscous solvent is sesame oil.

14. The preparation according to claim 1, wherein the active ingredient is incorporated into the biodegradable carrier in the following state:
  (i) the active ingredient is chemically bound to the carrier matrix,
  (ii) the active ingredient is bound to the carrier matrix by intermolecular action, or
  (iii) the active ingredient is physically embraced within the carrier matrix.

15. The preparation according to claim 1, wherein the active ingredient is selected from the group consisting of mitomycin, bleomycin, adriamycin, tespamin, indomethacin, 4-carbamoyl-5-hydroxyimidazole or a salt or hydrate thereof, prostaglandins, prostacyclines, tissue plasminogen activator, bio-hormones, interferons, interleukins, tumor necrosis factor, and other cytokines.

16. The preparation according to claim 1, wherein the active ingredient is selected from the group consisting of tissue plasminogen activator, prostaglandins, prostacyclines, bio-hormones, interferons, interleukins, tumor necrosis factor, and other cytokines.

17. The preparation according to claim 1, wherein the active ingredient is selected from the group consisting of interferons, interleukins, tumor necrosis factor, growth hormones, growth hormone releasing factor, somatomedines, calcitonin, macrophase activating factor, migration inhibitory factor, and colony stimulating factor.

18. The preparation according to claim 1, wherein the active ingredient is selected from the group consisting of interferons, growth hormones, growth hormone releasing factor, and somatomedines.

19. The preparation according to claim 10, wherein the viscous solvent for injection is a member selected from the group consisting of vegetable oils, polyethylene glycol, propylene glycol, silicone oil, and medium-chain fatty acid triglycerides.

20. The preparation according to claim 10, wherein the biodegradable carrier is a member selected from the group consisting of collagen, gelatin and a mixture thereof.

21. The preparation according to claim 15, wherein indomethacin is present in an amount of 0.5 to 500 mg per dosage unit.

22. The preparation according to claim 15, wherein interferon is present in an amount of $10^4$ to $10^9$ IU per dosage unit.

23. The preparation according to claim 15, wherein 4-carbamoyl-5-hydroxyimidazole or a salt or a hydrate thereof is present in an amount of 1 mg to 2 g per dosage unit.

24. The preparation according to claim 15, wherein the ratio of indomethacin to carrier is 0.005 to 1:1.

25. The preparation according to claim 15, wherein the ratio of interferon to carrier is $10^3$ to $10^8$ IU:1 mg.

26. The preparation according to claim 15, wherein the ratio of 4-carbamoyl-5-hydroxyimidazole to carrier is 0.01 to 1:1.

27. The preparation according to claim 1, further comprising stabilizers, preservatives, local anesthetic agents and formability agents.

28. The preparation according to claim 1, wherein the biodegradable carrier is a synthetic high molecular weight compound.

29. The preparation according to claim 1, wherein the biodegradable carrier is collagen.

30. The preparation according to claim 1, wherein the active ingredient is interferon.

31. The preparation according to claim 1, wherein the active ingredient is indomethacin.

32. The preparation according to claim 1, wherein the active ingredient is indomethacin and the carrier is collagen.

33. The preparation according to claim 1, wherein the active ingredient is indomethacin, the carrier is collagen, and the viscous solvent is sesame oil.

* * * * *